United States Patent
Albrektsson et al.

[11] Patent Number: 5,980,575
[45] Date of Patent: Nov. 9, 1999

[54] HIP JOINT PROSTHESIS

[75] Inventors: Bjorn Albrektsson; Magnus Jacobsson, both of Gothenburg; Lars Carlsson; Tord Rostlund, both of Kullavik; Stig Wennberg, Angered, all of Sweden

[73] Assignee: Astra Aktiebolag, Sodertalje, Sweden

[21] Appl. No.: 08/290,915
[22] PCT Filed: Feb. 26, 1993
[86] PCT No.: PCT/SE93/00169
§ 371 Date: Aug. 22, 1994
§ 102(e) Date: Aug. 22, 1994
[87] PCT Pub. No.: WO93/16663
PCT Pub. Date: Sep. 2, 1993

[30] Foreign Application Priority Data

Feb. 28, 1992 [SE] Sweden ................ 9200597

[51] Int. Cl.⁶ ........................................ A61F 2/36
[52] U.S. Cl. ................................ 623/23; 623/18
[58] Field of Search ................... 623/23, 18, 22; 606/62–63, 73, 89

[56] References Cited

U.S. PATENT DOCUMENTS

| | | | |
|---|---|---|---|
| 2,682,265 | 6/1954 | Collison | 623/23 |
| 2,685,877 | 8/1954 | Dobelle | 623/23 |
| 4,005,495 | 2/1977 | Locke et al. | 623/23 |
| 4,456,005 | 6/1984 | Lichty | 606/73 |
| 4,676,799 | 6/1987 | Legrand | 623/22 |
| 4,795,473 | 1/1989 | Grimes | 623/23 |
| 4,976,740 | 12/1990 | Kleiner | 623/23 |
| 5,007,935 | 4/1991 | Vincent et al. | 623/22 |
| 5,376,125 | 12/1994 | Winkler | 623/23 |
| 5,702,479 | 12/1997 | Schawalder | 623/23 |

FOREIGN PATENT DOCUMENTS

| | | | |
|---|---|---|---|
| 515003 | 11/1992 | European Pat. Off. | 623/23 |
| 2438470 | 5/1980 | France . | |
| 2674122 | 9/1992 | France | 623/23 |
| 2724234 | 12/1977 | Germany . | |
| 2854334 | 6/1980 | Germany . | |
| 3420035 | 5/1984 | Germany . | |
| 3607824 | 9/1987 | Germany | 623/23 |
| 9107932 | 6/1991 | WIPO . | |

Primary Examiner—Mickey Yu
Assistant Examiner—Bruce E. Snow
Attorney, Agent, or Firm—White & Case L.L.P.

[57] ABSTRACT

Hip joint prostheses are disclosed for permanent anchoring in the human hip joint of a ball unit in the neck of a human femur. The prosthesis include a first cylindrical fixture portion for extending from the collum femoris toward the outer side of the femur and a second cylindrical fixture portion for placement in the cancellus bone of the collum femoris, both of these portions including outer cylindrical surfaces with external self-tapping threads, and in which the first and second cylindrical fixture portions are joined into a single portion for insertion into a bore hole provided in the femur in a single operation.

14 Claims, 3 Drawing Sheets

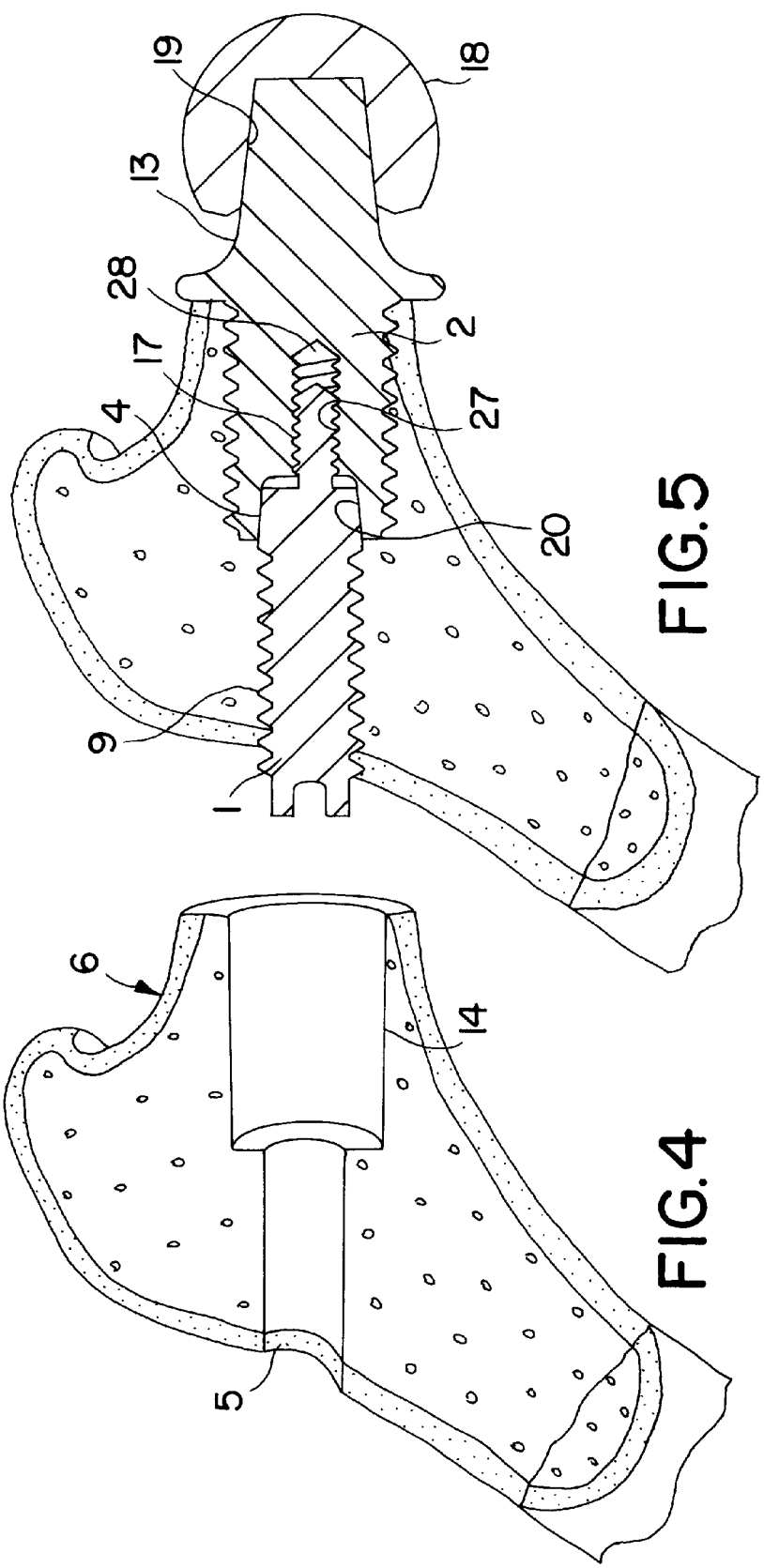

HIP JOINT PROSTHESIS

FIELD OF THE INVENTION

The present invention relates to a hip joint prosthesis for permanent anchoring in the human hip joint. More particularly, the present invention relates to such a prosthesis including an attachment part for a ball unit designed to be anchored in the neck of a human femur (collum femoris). Furthermore, this attachment part, which is intended to be inserted into a channel extending through the femoral collum, is provided with parts for carrying a ball or caput intended to be attached to the collum after removal of the head of the femur.

BACKGROUND OF THE INVENTION

The present invention relates to the development of a hip joint prosthesis of the kind disclosed in WO 89/11837. This document inter alia discloses a hip joint prosthesis comprising a primary fixture in the shape of a sleeve which is intended to be inserted into a central hole bored longitudinally through the collum femoris from the outer side of the femur and a secondary fixture in the shape of a cap having a spherical shape intended to be attached to and cover the end of the collum femoris when the head of the collum has been partially or entirely removed and the outside of the remaining end has been cut to a cylindrical shape. The primary and secondary fixtures are interconnected by means of a bolt which at one end has an internal thread. The bolt is to be inserted into the sleeve and its internal thread is to be made to engage a central, threaded stud projecting from the spherical cap. When the bolt is tightened, the cap is pressed over the cylindrically cut caput or end of the collum.

The prior art device thus is relatively complicated, both in terms of its construction and use.

In some applications, however, it may not be suitable to use this type of prior art device. One reason for this is that the shape of the collum may make it difficult to retain enough cortical bone to give the secondary fixture of cap a firm support, since the shape of the collum may vary to a great extent.

This prior device is also designed to be inserted in a two-step procedure; i.e., some parts of the prosthesis are to be inserted in a first operation, and the remaining parts are subsequently in a second operation after a healing period of a few months.

Other similar prior art is disclosed for instance in DE-A1-28 45 231, DE-A1-27 24 040, United U.S. Pat. No. 4,795,473 and U.S. Pat. No. 4,005,495.

The object of the present invention is to provide a hip joint prosthesis which is simple in construction and use and which is particularly suited for insertion in a one-step operation, and which can also be adapted to fit different conditions.

SUMMARY OF THE INVENTION

According to the present invention, this and other objects have been obtained by the discovery of an attachment part in a hip joint prosthesis of the type described above which also comprises a fixture comprising two main parts; namely, a first part which is to extend through a bore hole from the collum femoris towards the outer side of the femur and a second part which is intended to fit into a cylindrical cavity cut into the cancellus bone of the collum.

The fixture can be made in one piece but, in one preferred embodiment, comprises two separate parts which are firmly attached to each other before the fitting of the fixture into the femur.

This invention thus results in the cortical bone remaining intact to a larger degree, and the load conditions being such that a physiologically appropriate load on the upper part of the collum can be achieved. Forces can thus be transferred from the fixture to the femur without any noticeable movements by means of the direct or indirect contact with the inside of the cortical bone in the collum.

Further in accordance with the present invention, a hip joint prosthesis for permanent anchoring in the human hip bone has been provided which comprises attachment means for attaching a ball unit to be anchored in the neck of a human femur, the attachment means including a first cylindrical fixture portion for extending from the collum femoris toward the outer side of the femur and a second cylindrical fixture portion for placement in the cancellus bone of the collum femoris, both the first and second cylindrical fixture portions including outer cylindrical surfaces including external self-tapping threads, and including means for joining the first and second cylindrical fixture portions into a single fixture for insertion into a bore hole provided in the femur in a single operation.

In accordance with one embodiment of the hip joint prosthesis of the present invention, the attachment means includes a circumferential collar for abutting a cut end of the collum femoris.

In accordance with another embodiment to the hip joint prosthesis of the present invention, the first cylindrical fixture portion is selected to have a predetermined length corresponding to the distance from the collum femoris to the outer side of the femur. In another embodiment, the second cylindrical fixture portion is selected to have a predetermined diameter corresponding to a cylindrical countersunk cavity provided in the cancellus bone of the collum femoris. Preferably, the first cylindrical fixture portion has a first outer diameter and the second cylindrical fixture portion has a second outer diameter, and the second outer diameter is substantially greater than the first outer diameter.

In a highly preferred embodiment, the cylindrical countersunk cavity has a size corresponding to the second outer diameter which is selected so as to extend to a cortical bone of the femur in at least three locations, whereby the second outer diameter is such as to provide a second cylindrical fixture portion which abuts the cancellus bone in at least those three locations.

In accordance with another embodiment of the hip joint prosthesis of the present invention, the external self-tapping threads are right-handed. In another embodiment, however, the self-tapping threads are left-handed. Preferably, the circumferential collar is planar in configuration.

In accordance with another embodiment of the hip joint prosthesis of the present invention, the means for joining the first and second cylindrical fixture portions includes corresponding attachment means in separate first and second cylindrical fixture portions for firmly and tightly interconnecting the first and second cylindrical fixture portions. In a preferred embodiment, the means for forming the first and second cylindrical fixture portions into a single fixture comprises corresponding threaded portions in the first and second separate cylindrical fixture portions.

In accordance with another embodiment to the hip joint prosthesis of the present invention, the means for joining the first and second cylindrical fixture portions into a single portion comprises the first and second cylindrical fixtures being integral with each other.

BRIEF DESCRIPTION OF THE DRAWINGS

The present invention may be more fully appreciated with reference to the following detailed description, which refers, in turn, to the drawings, in which:

FIG. 4 is a side, elevational, sectional view of the recess in the collum; and

FIG. 5 is a side, elevational, sectional view of the fixture of the present invention within the recess in the collum.

DETAILED DESCRIPTION

Figure 1:
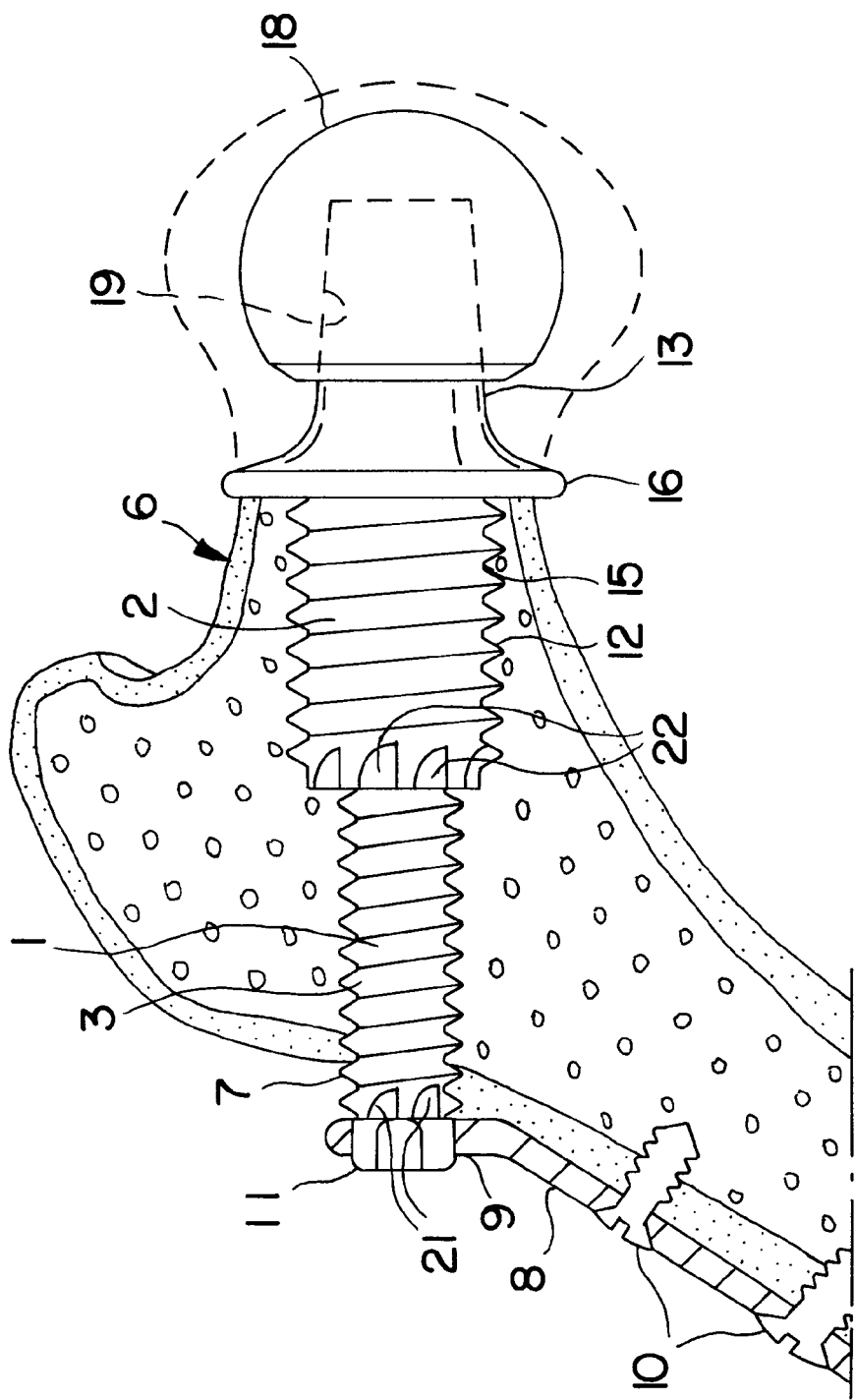
FIG. 1 is a side, elevational, partially sectional view of a femur with the fixture of the present invention mounted thereon.

Referring to the Figures, in which like reference numerals refer to like elements thereof, and as can be seen in FIGS. 1 and 5, the fixture comprises two main parts. These include an elongate, cylindrical first part 1 and a second plug-like, generally cylindrical part 2. The first part 1 is provided with relatively large and widely spaced threads 3 on a major or main part of its outer surface, with the remainder 4 of its outer surface being smooth and slightly conical. On the end surface of the slightly conical end of the first part 1 a narrow, threaded part 17 is located which is coaxial with the first part 1.

The first part 1 is adapted to fit in a channel or hole 5 drilled longitudinally and centrally through the collum 6. The head 7 of the first part 1 is to be located on the outside of the femur and may, but need not (cf FIG. 5), be locked against rotation by means of an elongated plate 8 having a recess 9 and with a shape which is complementary to the shape of the head 7 of the first part 1. The elongated plate 8 is attached to the femoral shaft by means of screws 10. The head 7 of the first part may, but again need not, also be covered by means of a nut 11 having threads which are complementary to the threads 3.

A longitudinal bore provided with threads is provided in the end surface or head 7 of the first part 1. This bore is complementary to a threaded tap on a guide rod having the same diameter as the first part.

The second part 2 is in the shape of a cylindrical plug. One part 12 of the plug is to be inserted into a recess 14 cut in the collum, cylindrically and co-axially with the channel or hole 5. The outer surface of the part 12 of the plug is provided with threads 15 similar to the threads 3 on the first part 1. The plug 12 is delimited by a circumferential flange 16 which thus limits insertion of the plug 12 into the cavity or recess 14. The plug 12 is also provided with a central hole 28 having two parts, namely an inner, threaded part 27 having an inner diameter corresponding to the outer diameter of the threaded narrow part 17 of the first part 1 and an outer, unthreaded part 20 which is slightly conically flaring in a manner corresponding to the unthreaded part 4 of the first part 1 of the fixture.

The threaded parts 17, 27 as well as the threaded parts 1, 12 may be right-handed or left-handed, depending on which side of the body they are to be mounted upon.

The threads on the first and second parts preferably are self-tapping. This can be achieved, for example, by the distal ends of the first and second part being provided with sharp-edged recesses 21, 22 in a manner similar to self-tapping screws. The recesses 22 on the second part 2 extend all the way to the end surface of the second part. The recesses 21 on the first part 1, however, do not extend all the way to the end surface or head 7, since this part of the first part 1 is normally intended to be located in the soft tissue and for this reason should not have any sharp edges. This is especially important if no covering nut 11 was used.

The first part 1 is made in several versions with different lengths and the second part 2 is made in several versions with different diameters of the plug part 12.

Finally, the plug is provided with a conical projection or attachment cone 13 for carrying the ball or caput 18, which is itself provided with a complementary conical hole 19.

The first and the second part of the fixture are preferably made of c. p. (commercially pure) titanium, and may be subjected to a suitable surface treatment. The elongated plate 8 is preferably made of a suitable titanium alloy, whereas its attachment screws 10 shall preferably be made of c. p. titanium, and have a diameter, for example, of about 4.5 mm. The attachment cone can be made of a titanium alloy or of c. p. titanium and should be treated in a suitable way in order to minimize the risk for fretting corrosion. The caput preferably should be made of a ceramic material, also in order to minimize the risk for fretting corrosion.

The socket or acetabulum is not part of the present invention, and may be of any commercially available type which is suitable for these purposes.

The operation for implanting the hip joint prosthesis is preferably performed in a one-stage operation. That operation is carried out as follows.

Any differences in the length of the legs are measured. An estimate of the narrowest diameter of the collum is then made in order to obtain an idea of the size of the implant to be used.

With great care not to disturb the blood circulation, the hip is exposed through an anteriolateral approach. The hip joint is then dislocated. A guide instrument for a cutting tool is attached. The caput is then cut off and removed.

The narrowest part of the collum is then measured directly in order to obtain further information regarding the size of the implant.

Figure 2:
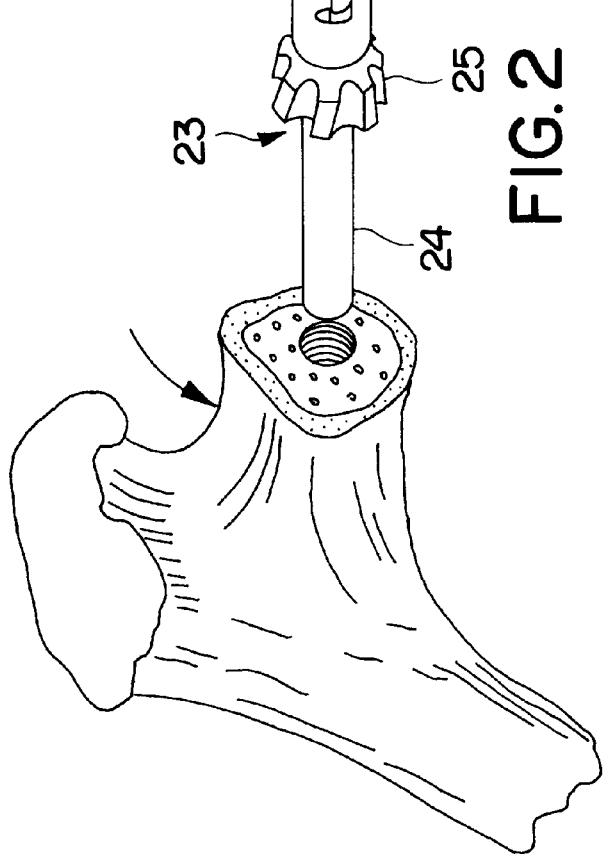
FIG. 2 is a side, perspective view of a combined reamer and cutter for shaping the recess in the collum for the fixture of the present invention.

A drill is then oriented by means of the guide instrument in such a way relative to the surface of the section that the drill is aligned with the longitudinal extent of the collum and is located at the center of a circle which touches the inside of the cortical bone in the section in at least three points. The diameter of this circle is determined. A hole 5 having a diameter corresponding to the diameter of the first part 1 is then drilled through the collum from the surface of the section, cf FIG. 2.

The cylindrical recess or hole 14 is then cut longitudinally in the collum from the direction of the caput by means of a rotary cutting (milling) tool 23. The cutting tool is provided in several sizes, each size corresponding to one size of a second part.

The cutting tool comprises a cylindrical, elongated guide part 24 which has a diameter corresponding to the diameter of the hole 5. The tool further comprises a reamer 25 which is coaxial with the guide part 24, the diameter thereof being chosen to correspond to the diameter of the above circle touching the cortical bone. The diameter and the length of the reamer also correspond to one of several standard sizes of the second part 2. Finally, the tool 23 also comprises a surface cutter 26.

Figure 3:
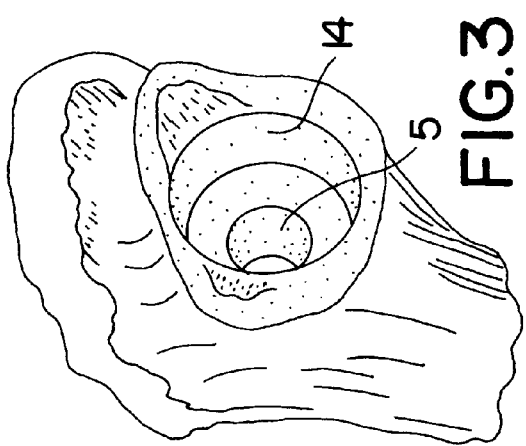
FIG. 3 is a front, elevational view showing the shape of the recess in the collum.

The guide 24 is then inserted into the hole 5 until the reamer 25 engages the surface of the section. The cylindrical recess 14 is then cut by means of the reamer until the surface cutter 26 engages and machines the surface of the section. The object of this machining is to ensure that the surface of the section is smooth and is oriented orthogonally relative to the longitudinal axis of the hole 5. This is important since the longitudinal direction of the collum is not necessarily orthogonal relative to the surface of the section. The resulting cavity 5, 14 can be seen in FIG. 3.

A first part having a suitable length and a second part having a suitable diameter are then chosen and attached to each other by means of the threaded part 17 on the first part 1 and the threaded hole 27 in the second part 2. The respective conically shaped parts 4, 20 on the first and the second part will ensure a secure and tight connection between the two parts.

The above-mentioned guide rod or extension, which has a diameter corresponding to the diameter of the hole 5, is then mounted on the free end of the first part 1 by means of the threaded bore therein. The guide rod is then inserted into the hole 5 until the threads on the first or the second part engage the bone tissue in the collum. The fixture is then screwed into the hole 5 and the recess 14, while being kept aligned by said guide, threads simultaneously being cut into the bone tissue on the inside of the hole 5 and the recess 14 in the collum until the flange or collar 16 abuts the cortical bone on the cut end surface of the collum. Due to the machining by means of the cutter 26, the flange or collar 16 will fit snugly against the surface of the section. The guide rod is then removed.

Finally, a ball or caput 18 is mounted on the attachment cone 13 and a reduction or repositioning of the joint is made in order to test the stability of the joint and the length of the leg. The length of the leg is corrected by using caputs having differently sized conical holes 19. The operation is then completed.

After the operation the hip joint can, in a relatively short time, be subjected to loads to a limited extent, since the design of the fixture will ensure that the fixture is stable to an extent which is sufficient to allow osseointegration.

The invention, of course, can be varied in many ways within the scope of the appended claims.

As mentioned above, the fixture can be made in one integral part, which may be advantageous in some applications even if it might greatly increase the number of different types to be kept in stock.

It is also possible to allow the first part of the fixture to end in the cancellus bone tissue before it reaches the cortical bone tissue on the outside of the femur, which may eliminate the necessity of disturbing the cortical bone and the soft tissue on the outer side of the femur.

It may not always be necessary to achieve the three-point contact between fixture and cortical bone in the collum femoris discussed above. This may be of particular importance if the collum femoris has such a shape that it more or less is impossible to obtain said three-point contact. In some cases it may also be more important to center or orient and size the fixture in such a way that a maximal bone contact is obtained. In one extreme it might also be conceivable to design or choose the first and second part of the fixture to have the same diameter. However, if the lateral femoral cortex is to be penetrated, the diameter of the first part should be kept at a minimum.

To express the advantages of the device somewhat differently, the hip joint prosthesis as set forth in the appended claims provides a cylindrical, longitudinal fixture which may be centered in the collum femoris. This allows a dimensioning of the device permitting a maximal bone contact, while at the same time minimizing the risk of perforating the cortical bone in the collum femoris. The fixture permits penetration of the lateral femoral cortex by means of a threaded extension thereof, which may have a smaller diameter than the rest of the fixture, which may have a flange or abutment collar which may be made to fit exactly against the cut end of the collum femoris by means of a guided bone cutting tool. The fixture can be positioned by means of a drill guide permitting the above centering in conjunction with a centering guide. This, in conjunction with a self-tapping design of the fixture, preferably in pure or almost pure titanium, allows the achievement of an optimal bone contact.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A fixture for a hip joint prosthesis which is adapted to be permanently anchored in an operational position in the neck of a human femur after resection of the femur head from the neck by translation of the fixture in a predetermined forward direction into a cylindrical bore having an open end in the femur neck outer surface exposed on resection of the femur neck and an axial extent in the predetermined forward direction from the open end towards the opposite outer surface of the femur below the greater trochanter, the fixture comprising:

a forward section which comprises a cylindrical forward portion of a first diameter and a coaxial cylindrical rearward portion of a second diameter greater than the first diameter and which after translation of the fixture to the operational position of the fixture is disposed in the cylindrical bore; and a rearward section connected to the cylindrical rearward portion of the forward section which is adapted in use to carry a prosthetic ball unit of the hip joint prosthesis and which after translation of the fixture to the operational position of the fixture is disposed outside of the bore in the femur neck, wherein the forward section is integrally formed such that the cylindrical forward and rearward portions of the forward section are rotatable and translate in unison when the forward section is translated to the operational position, and said portions are provided with external screw threads; and wherein the first and second diameters and external screw threads of the cylindrical forward and rearward portions of the forward section are adapted such that the fixture is able to be translated to the operational position by screwing of the fixture into the cylindrical bore about the predetermined forward direction with the external screw threads of the cylindrical forward and rearward portions simultaneously turning in the bone tissue forming the boundary wall of the cylindrical bore.

2. A fixture for a hip joint prosthesis which is adapted to be permanently anchored in an operational position in the neck of a human femur after resection of the femur head from the neck by translation of the fixture in a predetermined forward direction into a cylindrical bore having an open end in the femur neck outer surface exposed on resection of the femur neck and an axial extent in the predetermined forward direction from the open end towards the opposite outer surface of the femur below the greater trochanter, the fixture comprising:

a forward section which comprises a cylindrical forward portion of a first diameter and a coaxial cylindrical rearward portion of a second diameter greater than the first diameter and which after translation of the fixture to the operational position of the fixture is disposed in the cylindrical bore; and a rearward section connected to the cylindrical rearward portion of the forward section which is adapted in use to carry a prosthetic ball unit of the hip joint prosthesis and which after translation of the fixture to the operation position of the fixture is disposed outside of the bore in the femur neck, wherein the forward section is integrally formed such that the cylindrical forward and rearward portions of the forward section are rotatable and translate in unison when the forward section is translated to the operational position, and said portions are provided with external screw threads; and wherein the first and second diameters and external screw threads of the cylindrical forward and rearward portions of the forward section are adapted such that the fixture is able to be translated to the operational position by screwing of the fixture into the cylindrical bore about the predetermined forward direction with the external screw threads of the cylindrical forward and rearward portions simultaneously turning in the bone tissue forming the boundary wall of the cylindrical bore, wherein the second diameter is selected such that when the fixture is in the operational position the external screw threads of the cylindrical rearward portion of the forward section register in cortical bone at the outer peripheral surface of the femur neck which forms at least a part of the adjacent boundary wall of the cylindrical bore, and wherein the first diameter is selected such that when the fixture is in the operation position the external screw threads of the cylindrical forward portion of the forward section register in cancellous bone which forms the adjacent boundary wall of the cylindrical bore.

3. A fixture for a hip joint prosthesis which is adapted to be permanently anchored in an operational position in the neck of a human femur after resection of the femur head from the neck by translation of the fixture in a predetermined forward direction into a cylindrical bore having an open end in the femur neck outer surface exposed on resection of the femur neck and an axial extent in the predetermined forward direction from the open end towards the opposite outer surface of the femur below the greater trochanter, the fixture comprising:

a forward section which comprises a cylindrical forward portion of a first diameter and a coaxial cylindrical rearward portion of a second diameter greater than the first diameter and which after translation of the fixture to the operational position of the fixture is disposed in the cylindrical bore; and a rearward section connected to the cylindrical rearward portion of the forward section which is adapted in use to carry a prosthetic ball unit of the hip joint prosthesis and which after translation of the fixture to the operational position of the fixture is disposed outside of the bore in the femur neck, wherein the forward section is integrally formed such that the cylindrical forward and rearward portion of the forward section are rotatable and translate in unison when the forward section is translated to the operational position, and said portions are provided with external screw threads; and wherein the first and second diameters and external screw threads of the cylindrical forward and rearward portion of the forward section are adapted such that the fixture is able to be translated to the operational position by screwing of the fixture into the cylindrical bore about the predetermined forward direction with the external screw threads of the cylindrical forward and rearward portions and simultaneously turning in the bone tissue forming the boundary wall of the cylindrical bore, and wherein the cylindrical forward portion of the forward section of the fixture is releasably securable to the cylindrical rearward portion of the forward section.

4. A fixture as claimed in claim 1, 2 or 3 wherein the rearward section comprises a rearward portion adapted to carry the prosthetic ball unit and a radially outwardly extending flange forward portion connected to the rearward portion of the cylindrical forward section, the flange forward portion abutting the peripheral edge of the open end of the bore in the femur neck outer surface when the fixture is in the operational position to delimit the translation of the fixture in the predetermined forward direction.

5. A fixture as claimed in claim 4 wherein the rearward portion of the rearward section has an outer surface profile of a truncated cone which tapers outwardly in the predetermined forward direction for sealing engagement in a complementary conical recess in the prosthetic ball unit.

6. A fixture as claimed in claim 1, 2 or 3 wherein the axial length of the cylindrical forward section of the fixture is selected such that when the fixture is in the operational position the forward end of the forward portion of the cylindrical forward section protrudes from an open end of the bore in the outer surface of the femur below the greater trochanter.

7. A fixture as claimed in claim 3 wherein the length of the forward portion of the cylindrical forward section of the fixture is selected such that when the fixture is in the operational position the forward end of the forward portion of the cylindrical forward section protrudes from an open end of the bore in the outer surface of the femur below the greater trochanter.

8. A fixture as claimed in claim 3, wherein the rearward portion of the cylindrical forward section of the fixture is provided with an internally threaded bore and the forward portion of the cylindrical forward section of the fixture is provided with an externally threaded protrusion for screwing into the internally threaded bore to secure the forward portion to the rearward portion.

9. A fixture as claimed in claim 1, 2 or 3 wherein the cylindrical forward section is provided with self-tapping screw threads.

10. A fixture as claimed in claim 9 wherein the self-tapping screw threads are provided with sharp-edged recesses.

11. A fixture as claimed in claim 2 wherein the second diameter of the cylindrical forward section is selected such that the screw threads thereof are adapted to register in cortical bone in at least three discrete circumferentially spaced locations of the boundary wall of the bore.

12. A fixture as claimed in claim 1 or 2 wherein the cylindrical forward portion of the forward section is releasably securable to the cylindrical rearward portion of the forward section.

13. A hip joint prosthesis including a fixture according to claim 1, 2 or 3.

14. A hip joint prosthesis including a fixture according to claim 1, 2 or 3 wherein the prosthesis further comprises a ball unit adapted in use to be fitted to the rearward section of the fixture.

\* \* \* \* \*